United States Patent [19]

Wilk

[11] Patent Number: 5,191,902
[45] Date of Patent: Mar. 9, 1993

[54] PROPHYLACTIC DEVICE

[76] Inventor: Peter J. Wilk, 185 W. End Ave., New York, N.Y. 10023

[21] Appl. No.: 816,461

[22] Filed: Jan. 3, 1992

[51] Int. Cl.⁵ .................................................. A61F 5/00
[52] U.S. Cl. ........................................ 128/844; 128/918
[58] Field of Search ..................... 128/842, 844, 918; 604/346, 347, 349

[56] References Cited

U.S. PATENT DOCUMENTS

| | | | |
|---|---|---|---|
| 2,586,674 | 2/1952 | Lonne | 128/844 |
| 4,638,790 | 1/1987 | Conway et al. | 128/844 |
| 4,792,849 | 12/1989 | Park et al. | 128/842 |
| 4,798,600 | 1/1989 | Meadows | 128/844 X |
| 4,898,184 | 2/1990 | Skurkovich et al. | 128/844 |
| 4,910,803 | 3/1990 | Cukier | 128/844 X |
| 4,919,149 | 4/1990 | Stang | 128/842 |
| 4,930,522 | 6/1990 | Busnel et al. | 128/844 |
| 4,961,734 | 10/1990 | Kassman | 128/844 X |
| 4,984,582 | 1/1991 | Romaniszyn et al. | 128/844 |
| 5,050,619 | 9/1991 | Ferguson | 128/842 X |

Primary Examiner—Robert A. Hafer
Assistant Examiner—Sam Rimell
Attorney, Agent, or Firm—R. Neil Sudol; Henry D. Coleman

[57] ABSTRACT

A prophylactic device comprises an outer condom having a circular base, and an inner condom inserted inside the first condom and also having a circular base. The device further comprises a heat seal attaching the outer condom and the inner condom to one another about their respective bases. The outer condom is provided in a region about its base with a plurality of openings disposed in an annular array for permitting the evacuation of air from between the first condom and the second condom during use of the device.

10 Claims, 1 Drawing Sheet

U.S. Patent    Mar. 9, 1993    5,191,902
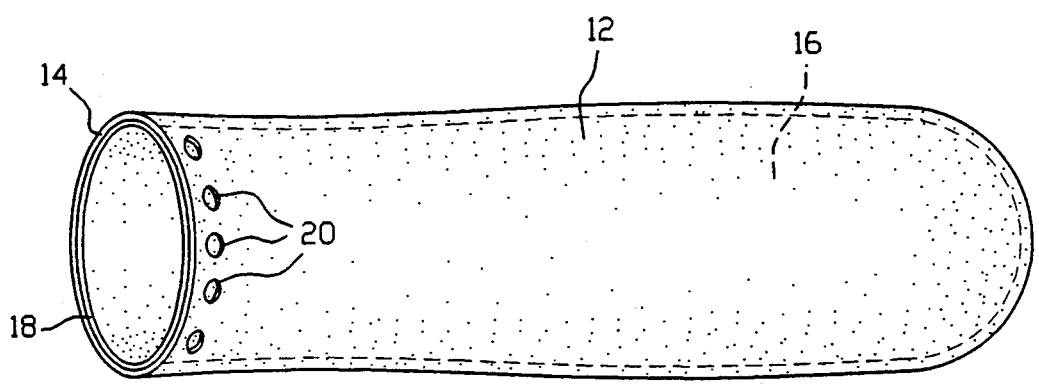

PROPHYLACTIC DEVICE

BACKGROUND OF THE INVENTION

This invention relates to a prophylactic device. More particularly, this invention relates to an improved condom.

In this day of dreaded venereal diseases and sexual freedom, people have been increasingly urged by the medical profession, as well as by governmental organizations, to use condoms to prevent the spread of venereal diseases.

However, condoms are well known to be only partially effective. Leakage and breakage both serve to reduce the effectiveness of condoms as a barrier to contagion and to conception.

OBJECTS OF THE INVENTION

An object of the present invention is to provide an improved condom.

Another object of the present invention is to provide a condom which increases the effectiveness of the device as a barrier to the spread of disease.

Another, more particular, object of the present invention is to provide such a condom which is not prohibitively expensive.

SUMMARY OF THE INVENTION

A prophylactic device comprises, in accordance with the present invention, a first condom having a first base, and a second condom inserted inside the first condom, the second condom having a second base. The device further comprises means for attaching the first condom and the second condom to one another about their respective bases. In addition, the first condom is provided in a region about the first base with an opening for permitting the evacuation of air from between the first condom and the second condom during use of the device.

Pursuant to another feature of the present invention, the first condom is provided with a plurality of openings in the region about the first base. The openings are advantageously spaced from each other in an annular array at the base of the outer condom.

The outer and inner condoms may be attached to one another about their respective bases via a heat seal.

An improved prophylactic in accordance with the present invention may be rolled in the manner of conventional condoms for transport and sale.

A condom in accordance with the present invention increases the effectiveness of the condom as a barrier to the spread of disease. Moreover, such a condom is not prohibitively expensive to manufacture.

BRIEF DESCRIPTION OF THE DRAWING

The sole FIGURE of the drawing is a schematic side elevational view of a prophylactic device in accordance with the present invention.

DETAILED DESCRIPTION

As illustrated in the drawing, a prophylactic device comprises an outer condom 12 having a circular base or rim 14 and an inner condom 16 inserted inside the outer condom. Inner condom 16 likewise has a circular base 18 defining an opening for the insertion of a penis (not illustrated). Outer condom 12 and inner condom 16 are attached to one another in an annular seam about their respective bases 14 and 18. In addition, outer condom 12 is provided in a region about base 14 with a plurality of openings 20 spaced from each other in an annular array for permitting the evacuation of air from between the outer condom and inner condom 16 during use of the device.

Outer condom 12 and inner condom 16 are attached to one another about their respective bases 14 and 18 via an annular heat seal.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

What is claimed is:

1. A prophylactic device comprising:
   a first condom having a first base, said condom being closed at an end opposite said base;
   a second condom inserted inside said first condom, said second condom having a second base, said second condom being open at said second base and closed at an end opposite said second base; and
   means for attaching said first condom and said second condom to one another about their respective bases, said first condom being provided in a region about said first base with an opening for permitting the evacuation of air from between said first condom and said second condom during use of the device.

2. The device defined in claim 1 wherein said first condom is provided with a plurality of openings in said region about said first base.

3. The device defined in claim 2 wherein said openings are spaced in an annular array at said first base.

4. The device defined in claim 1 wherein said means for attaching includes a heat seal.

5. The device defined in claim 1 wherein said means for attaching connects said first condom to said second condom along an annular seam.

6. A prophylactic device comprising:
   a first condom having an open end and a closed end; and
   a second condom having a closed end and an annular rim at an end opposite such closed end, said first condom being inserted inside said second condom so that said first condom and said second condom are essentially co-extensive with one another, said first condom being attached about said open end to said second condom in a region thereof about said rim, said second condom being provided proximately to said rim with an opening for permitting the evacuation of air from between said first condom and said second condom during use of the device.

7. The device defined in claim 6 wherein said first condom is provided with a plurality of openings proximately to said rim.

8. The device defined in claim 7 wherein said openings are spaced in an annular array.

9. The device defined in claim 6 wherein said means for attaching connects said first condom to said second condom along an annular seam.

10. The device defined in claim 6 wherein said means for attaching includes a heat seal.

* * * * *